United States Patent
Bussolati

(10) Patent No.: US 11,204,305 B2
(45) Date of Patent: Dec. 21, 2021

(54) ACID FREE GLYOXAL AS FIXATIVE FOR HISTOLOGICAL PREPARATIONS

(71) Applicant: ADDAX BIOSCIENCES S.R.L., Turin (IT)

(72) Inventor: Giovanni Bussolati, Turin (IT)

(73) Assignee: ADDAX BIOSCIENCES S.R.L., Turin (IT)

( * ) Notice: Subject to any disclaimer, the term of this patent is extended or adjusted under 35 U.S.C. 154(b) by 263 days.

(21) Appl. No.: 16/075,149

(22) PCT Filed: Feb. 10, 2017

(86) PCT No.: PCT/EP2017/053041
§ 371 (c)(1),
(2) Date: Aug. 3, 2018

(87) PCT Pub. No.: WO2017/140596
PCT Pub. Date: Aug. 24, 2017

(65) Prior Publication Data
US 2019/0049348 A1  Feb. 14, 2019

(30) Foreign Application Priority Data
Feb. 18, 2016  (IT) .................. 102016000016894

(51) Int. Cl.
*G01N 1/30* (2006.01)
*G01N 33/48* (2006.01)
*A01N 1/00* (2006.01)

(52) U.S. Cl.
CPC .............. *G01N 1/30* (2013.01); *A01N 1/00* (2013.01); *G01N 33/48* (2013.01); *G01N 2001/307* (2013.01)

(58) Field of Classification Search
CPC ..... G01N 1/30; G01N 33/48; G01N 2001/307
See application file for complete search history.

(56) References Cited

U.S. PATENT DOCUMENTS

| | | | | |
|---|---|---|---|---|
| 3,897,503 | A | * | 7/1975 | Wessendorf .................. 568/599 |
| 5,439,667 | A | * | 8/1995 | Camiener ................ A01N 1/00 424/75 |
| 7,368,132 | B2 | * | 5/2008 | Rocha ...................... G01N 1/30 424/641 |
| 2017/0336303 | A1 | * | 11/2017 | Chafin ..................... G01N 1/30 |

OTHER PUBLICATIONS

Dapson RW, "Glyoxal fixation: how it works and why it only occasionally needs antigen retrieval", Biotechnic and Histochemistry, vol. 82, No. 3, Jan. 1, 2007, pp. 161-166.
Gehin N., Le glyoxal: un possible substitut du formaldehyde en anatomie pathologique?—Theses doctorale:, Jun. 13, 2008, pp. 1-207.
International Search Report and Written Opinion of PCT/EP2017/053041 dated Jul. 14, 2017.
Partial International Search of PCT/EP2017/053041 dated May 19, 2017.
Sabatini D.D., et al., "Cytochemistry and electron microscopy: the preservation of cellular ultrastructure and enzymatic activity by aldehyde fixation", The Journal of Cell Biology, vol. 17, No. 1, Apr. 1, 1963, pp. 19-58.
Want Y., et al., "Histomorphometric comparison after fixation with formaldehyde or glyoxal", Biotechnic and Histochemistry, vol. 86, No. 5, Sep. 21, 2010, pp. 359-365.

* cited by examiner

*Primary Examiner* — Quang Nguyen
(74) *Attorney, Agent, or Firm* — Silvia Salvadori, P.C.; Silvia Salvadori

(57) ABSTRACT

The invention refers to a composition for the fixation of histological preparations, comprising a solution of glyoxal, wherefrom acids, normally present in the commercially available glyoxal, have been removed. The composition of the invention provides an optimal fixative for the preservation of structure, antigenic components and nucleic acids in tissues. The acid-free glyoxal has limited toxicity, is not considered as a carcinogenic agent and represents a valid alternative to formalin for the fixation of tissues and cells.

4 Claims, 5 Drawing Sheets

Specification includes a Sequence Listing.

ACID FREE GLYOXAL AS FIXATIVE FOR HISTOLOGICAL PREPARATIONS

This application is a U.S. national stage of PCT/EP2017/053041 filed on 10 Feb. 2017, which claims priority to and the benefit of Italian Application No. 102016000016894 filed on 18 Feb. 2016, the contents of which are incorporated herein by reference in their entireties.

The invention refers to a composition for the fixation of histological and cytological preparations, comprising a solution of glyoxal free of acids.

INTRODUCTION

Preservation and fixation of histological tissues is currently made with a water solution containing formaldehyde, and specifically a solution containing 4% formaldehyde in water, known as formalin.

The use of formalin is very extensive in the industry, for the production of resins and the fixation of leather and, in the medical field, for the transfer of tissues, for their preservation (for instance in museums) and for the fixation in histology. This must precede the embedding in paraffin, the sectioning and staining of histological preparations in order to allow the microscopic examination for the histological diagnosis (Fox et al. Formaldehyde fixation. J. Histochem. Cytochem, 33, 845-853, 1985).

The use of formalin is world-wide: in Italy alone, the consumption is in the order of millions of litres. Therefore, the use of formalin involves technicians and nurses, as well as pathologists which are exposed to the use of formalin and to inhalation of formaldehyde vapours.

The toxicity of formaldehyde is known since long time: it is an allergenic and toxic substance which can cause eczemas of the skin and respiratory asthma and it is classified as carcinogenic. Despite the fact that formaldehyde is still considered as the fixative of choice (Buesa R J. Annals of Diagnostic Pathology 12 (2008) 387-396)), its use causes problems.

Environmental authorities are increasingly concerned in view of the toxicity of this volatile reagent, so that a banning of formalin from 2016 has been proposed in the European countries, as a consequence of the EC Regulation n. 605/2014 of May 6, 2014 that modifies the EC Regulation n. 1272/2008. This decision, while justified by the definition of this reagent as a carcinogen (category 1B/2) and mutagen, might exert a heavy and perhaps unacceptable impact on diagnostic pathology. Reaction to this situation is presently limited to adoption of protective procedures, designed to prevent excessive exposure to formaldehyde vapours, but no doubt the situation could only be solved by the adoption of non-toxic fixatives alternative to formalin.

A number of fixatives alternative to formalin have been proposed (Buesa R J., quoted above; Zanini et al. Environmental Health 2012, 11:59) but none of these has yet proved to provide a fast and satisfactory fixation.

The use of glyoxal (oxalic aldehyde) as an alternative to formalin for tissue fixation was originally proposed by Wicks e Suntzeff (Wicks L F and Suntzeff V. Science, 98, 204, 1943). Such bi-functional reagent tends to form polymers in solution and to form intra- and inter-molecular cross-links in proteins (Hopwood D. Histochemie, 20, 127-132, 1969). In solution, glyoxal results in various hydrated forms, the most common of which is the cyclic dimer 1.3 dioxo lane, formed at room temperature (Dapson R W. Biotechnic & Histochemistry 2007, 82(3): 161_166). Glyoxal, having a very low vapour pressure, does not give origin to vapours, even at relatively high temperatures (25-60° C.) and is thus free of risks of vapour inhalation (Anon. 1986, Glyoxal, a Technical Brochure. American Cyanamid Company, Wayne, N.J. 50 pp.).

Numerous studies have been made on the use of this substance as a histological fixative (Sabatini et al., *J Cell Biol.* 1963 April; 17:19-58). The use of a mixture of glyoxal with zinc salts or with alcohol so as to improve the results of histological fixation was described in U.S. Pat. No. 7,368,132 and in CA 2119554, respectively.

However, several studies confirmed that glyoxal does not guarantee a satisfactory morphological preservation similar to that produced by formalin (Buesa R J., Annals of Diagnostic Pathology 12 (2008) 387-396; Marcon et al., Annales de Pathologie 29, 460-467; 2009). Even the numerous formulations available in the market as fixatives alternative to formalin, which contain glyoxal added to other substances such as ethanol, methanol or metals (zinc), did not give satisfactory results and none of them met the favour of histologists. In the study of Marcon et al., the Authors compared the fixative properties of various solutions based on glyoxal with a solution of formaldehyde as reference. Comparing the results related to the various parameters under evaluation (morphological preservation, preservation of nucleic acids etc.), the solutions based on glyoxal resulted far worse than formalin. The Authors concluded that the glyoxal-based solutions cannot be recommended because of deleterious effects such as lysis of erythrocytes (Buesa, 2008; Macon et al, 2009) or the dissolution of microcalcifications (Umlas J. and Tulecke M T., Human Pathology 35, 1058-62, 2004). In addition, fluorescence in situ hybridization (FISH) analysis resulted in technically unacceptable results (Tubbs R R, Hsi E D, Hicks D, Goldblum J. Am J Surg Pathol 2004; 28(3):417-419; Willmore-Payne C, Metzger K, Layfield L J. Appl Immunohistochem Mol Morphol 2007; 15(1):84-87) and extraction and sequencing nucleic acids proved unsatisfactory (Gillespie J W, Best C J, Bichsel V E, Cole K A, Greenhut S F, Hewitt S M, et al. Am J Pathol 2002; 160(2):449-457). Such effects are produced by glyoxal-based fixatives in commerce. The exact composition of these reagents is not known but they include glyoxal, ethanol, methanol and zinc.

All of these proprietary fixatives (Glyo-Fix®, Shandon; Histo-Fix®, Bioworld; Histo-CHOICE®, Amresco; Preserve®, Anatech and Safe-Fix II®, Fisher Scientific) are reportedly acidic (in the range of pH 4). Marcon et al (2009) and Gehin-Marcon N. (Thesis discussed on 13 Jun. 2008, l'Universitè de Nancy) tried different solutions of glyoxal in phosphate buffer at different pH, but the study was mainly made on a glyoxal solution at pH 4. Specifically, Gehrin-Marcon (2008) in her thesis mentions (Discussion, pages 142-143) that" We have seen in our early works (trials) that 4% glyoxal at pH 7 was a bad histological fixative, not allowing a good preservation of micro-anatomy. The addition of a small percentage of ethanol (10%) and acidification of the solution (pH 4) allow to obtain better results". It should be noted that the thesis does not specify if the fixative prepared by adding commercial 4% glyoxal to a pH 7 buffer was used immediately after preparation or thereafter and if the final pH of the fixative was checked (the solution is unstable over time). Moreover, no information is given on the pH of the solution at the moment of use. In addition, the acids were not removed from the glyoxal solution. This issue will be addressed to in the description of the invention, especially example 5.

DESCRIPTION OF THE INVENTION

It has now been surprisingly found and contrary to previous studies that the properties of glyoxal as fixing agent can be significantly improved by removing its content of acids.

The glyoxal which is currently available as a pure reagent (glyoxal, 40 wt % solution in water, Code N. 128465, Sigma Aldrich, Milano) has in fact a strongly acid pH (around pH 4) because of the presence of glyoxylic, oxalic, glycolic, acetic and formic acids, formed as a consequence of degradation and oxidation of the aldehyde moiety, during and progressively after the preparation of glyoxal (Zhiyong Zhang, Dishun Zhao and Baoyun Xu, Journal of Chromatographic Science 2013; 51:893-898). Neutralization of these acids can be obtained using strong bases (NaOH) or removal can be obtained using ion exchange resins. The reagent thus obtained, here defined as Glyoxal Acid-Free (G.A.F.) in a water solution with a defined concentration turned out to be a histological fixative with superior qualities in the preservation of cells and tissues.

The present invention regards therefore the use of acid-free glyoxal free as an histological fixative.

The invention refers as well to a kit for the fixation of histological tissues including a container of the "bag-in-box" type or bags under-vacuum containing the fixative of the invention or other reagents (stains, buffers and other reagents of common use in histology).

As compared to formalin, the fixative of the invention not only does not release toxic vapours (contrary to formaldehyde) but it is also fast, penetrates rapidly into tissues and produces a preservation of tissue and cell features similar to those present in vital conditions.

DETAILED DESCRIPTION OF THE INVENTION

Figure 1:
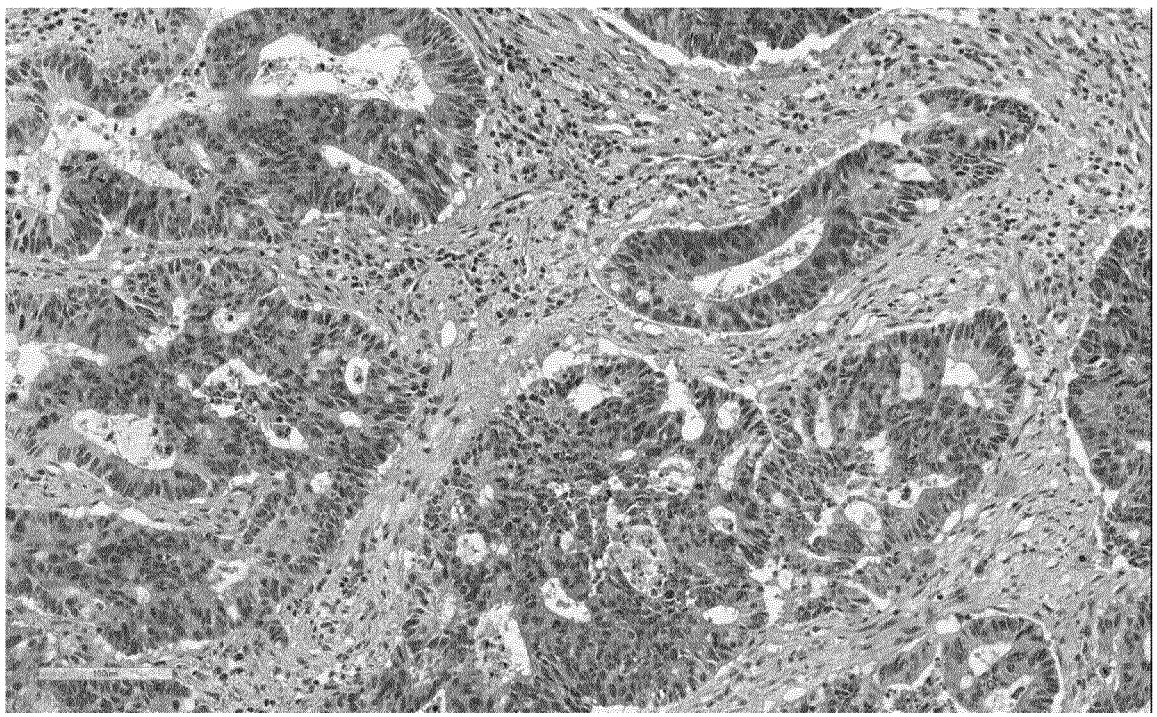
FIG. 1 shows a carcinoma of the colon after fixation with Acid Free Glyoxal.

The term "acid-free glyoxal" refers to a water solution of glyoxal with a concentration by weight variable between 0.1 and 90%, preferably from 1.5 to 50%, more preferably from 2 to 20%, having a pH from 7.1 to 8.0, preferably 7.2-7.4. A 2% solution having a pH 7.3±0.2 is particularly preferred.

The solution according to the invention, for use as histological and cytological fixative, can be prepared from commercially available solution of glyoxal 40%, by removing the content of acids with an ion exchange resin or by neutralization with ammonia, alkaline hydroxides, carbonates or bicarbonates such as NaOH, KOH, sodium, calcium, zinc or barium carbonates.

Examples of the procedures to eliminate acids are reported.

Removal of Acids by Means of Ion-Exchange Resins.

30 g of ion-exchange resin Bio-Rad AG 501-X8 (Bio-Rad; Milan) were added to 150 ml of a solution of commercial 40% glyoxal (Sigma). After 60', the complex was filtered so as to obtain 150 ml of a clear solution. Distilled water or saline solution (NaCl 0.9%) was added to this liquid to a concentration of 2% w/w of glyoxal. The pH of this solution resulted to be around neutrality, thus confirming the removal of acids produced by the ion-exchange resin.

By adding the acid-free glyoxal to a Phosphate buffer 0.1M pH 7.2, a 2% solution of glyoxal with a pH still kept at 7.2 was obtained.

In a similar way, using a strongly basic ion-exchange resin (Amberlite® IRA-400 chloride form; Sigma, Milano), by following the above procedure, the complete removal of acids from the solution of glyoxal was achieved. Said 2% glyoxal solution in saline solution or in phosphate buffer gave origin to reagents used as histological fixatives.

On the contrary, when the strongly acid commercial glyoxal (Sigma) was added to 0.1M Phosphate buffer pH 7.0 or 7.2, to a final concentration of 2% or 4%, the resulting solution became very acidic, well below neutrality.

100 ml of a 40% solution of glyoxal deprived of acids by means of ion-exchange resins were kept at room temperature. After 1 week the pH of this solution, initially around neutrality, decreased gradually and reached a pH 4.8, as a result of the oxidation of glyoxal to glyoxylic acid.

This process of acidification resulted in fixatives with a poor preservation of the structure and components of tissues.

This means that after the acids have been removed from the solution of glyoxal, oxidation of the reagent leading to formation of acids has to be prevented.

This can be obtained by the use of the following procedures (optionally, combined): a) use of containers preventing the contact of the solution with air, or b) keeping the solution frozen until to use or c) adding anti-oxidants such as ascorbic acid or sulphides or alcohols such as ethanol.

a) The technology "bag in box", currently used to preserve wine and to prevents exposure to air was proposed by William Scholle in 1955. The liquid is introduced in a plastic box, then the bag is closed with a tap and the air present is completely eliminated. The bag is then introduced into a box wherefrom the tap is put outside. The uptake of liquid involves the reduction in volume of the bag, but prevents the entrance of air.

As an example, 3 litres of a 2% solution of Acid-free Glyoxal pH 7.1 was introduced into "bag in box" (Ondulati e Imballaggi del Friuli spa, Villesse, Gorizia). Liquid was extracted from this container as a fixative and the pH was constantly checked. After 6 months, the pH of the solution was still kept above pH 7, thus confirming the absence of acidification due to oxidation.

As an alternative, always with the goal of preventing the contact with air and hence oxidation of glyoxal, 1000 ml of a 2% solution of acid-free glyoxal (pH 7.3) were introduced into a plastic bag Seal-SAFE, (Milestone, Soresole (BG), Italy) and then the under vacuum procedure was applied using the apparatus Tissue-SAFE (Milestone). After 6 months the pH was still above 7, confirming the absence of acidification due to oxidation.

b) the solution of Acid-free Glyoxal, added or not to buffering solutions such as phosphate buffer pH 7.2-7.4, preferentially 7.3, maintains stable if frozen at a temperature between −1° and −80°, preferentially at −20° C. The liquid, once frozen, does not undergo oxidation and acidification and, once thawed, can be used for fixation.

c) In order to prevent oxidation of glyoxal and thus its acidification (with decrease of the pH below neutrality and thus worsening of the quality of fixation) anti-oxidizing agents such as ascorbic acid (Sigma) were added in percentage from 0.01 to 20%, preferably 1%, and/or trimethylphenol (Sigma) in a percentage from 0.01 to 20%, preferably 0.1%, or alcohols such as ethanol (Carlo Erba, Milan) in a percentage from 1% to 90%.

Specifically, a solution of 20% Acid-Free Glyoxal in ethanol 50% maintains a pH around neutrality for several months.

In addition, we have also observed that other reagents, such as ethylene glycol and polyethylene glycol, in concentrations ranging between 0.1 and 50%, preferentially 5%, were effective in preventing acidification of glyoxal solutions, over time.

The following Examples illustrate the invention in more detail.

Example 1

Tissue samples (from 20 cases of wall of large intestine, of carcinomas of the colon, of carcinomas of the breast were collected in excess of the diagnostic purposes.

The fragments, fresh from the operating theatre, had a thickness of 3-4 mm and were similar to those currently employed for diagnostic purposes. The samples, embedded in cassettes, were immersed at room temperature in the fixation liquid.

From the same case, samples taken in parallel were immersed in 3 different types of fixative: 1) Phosphate buffered formalin (PBF) (Diapat, Bergamo), 2) commercial 2% glyoxal (Sigma, Milano) dissolved in phosphate buffer pH 7.2 (the pH of this solution was then checked and the final pH was 6.5; 3) Acid Free Glyoxal 2% in phosphate buffer pH 7.3.

The fixation, at room temperature, was for 3 or 24 hours, then the cassettes were routinely processed by alcohol dehydration and paraffin embedding using a Leica Processor (Leica, Milano).

Histological sections were obtained from the paraffin blocks and stained in parallel with Haematoxylin-Eosin.

Immunohistochemical staining was performed on sections of fragments fixed in Formalin (preparation 1) and in Acid-Free Glyoxal (preparation 3) for the following antigens: Cytokeratin large spectrum; Cytokeratin 19; CDX2 and Ki67. On parallel section, FISH staining was also performed for the ALK and HER2 genes.

Results.

At microscopic examination, tissues fixed in Preparation 2, i.e. in a commercial 2% glyoxal solution, final pH 6.5, showed the drawbacks linked to fixation in glyoxal as described in the literature (Dapson, 2007; Buesa, 2008; Macon et al, 2009), that is: cohartation of tissues with presence of shrinkage between epithelium and stroma, lysis of the erythrocytes, clear nuclei, with loss of nucleic material.

On the contrary, tissues fixed in Acid-Free Glyoxal (preparation 3) showed an optimal fixation, devoid of the defects above listed and similar to that obtained in tissues fixed in Formalin (Prep. 1).

The immuno-histochemical reactions for Cytokeratins L:S:, for Cytokeratin 19, for CDX2 and Ki67, performed in parallel in tissues fixed in formalin and in Acid-Free Glyoxal gave basically the same results.

In all similarity, the FISH reactions for ALK and HER2 gave similar reactions.

FIG. 1. Carcinoma of the colon. Fixation with Acid Free Glyoxal. Staining with Haem.-Eosin. The better preservation of cells and tissues is evident.

Figure 2:
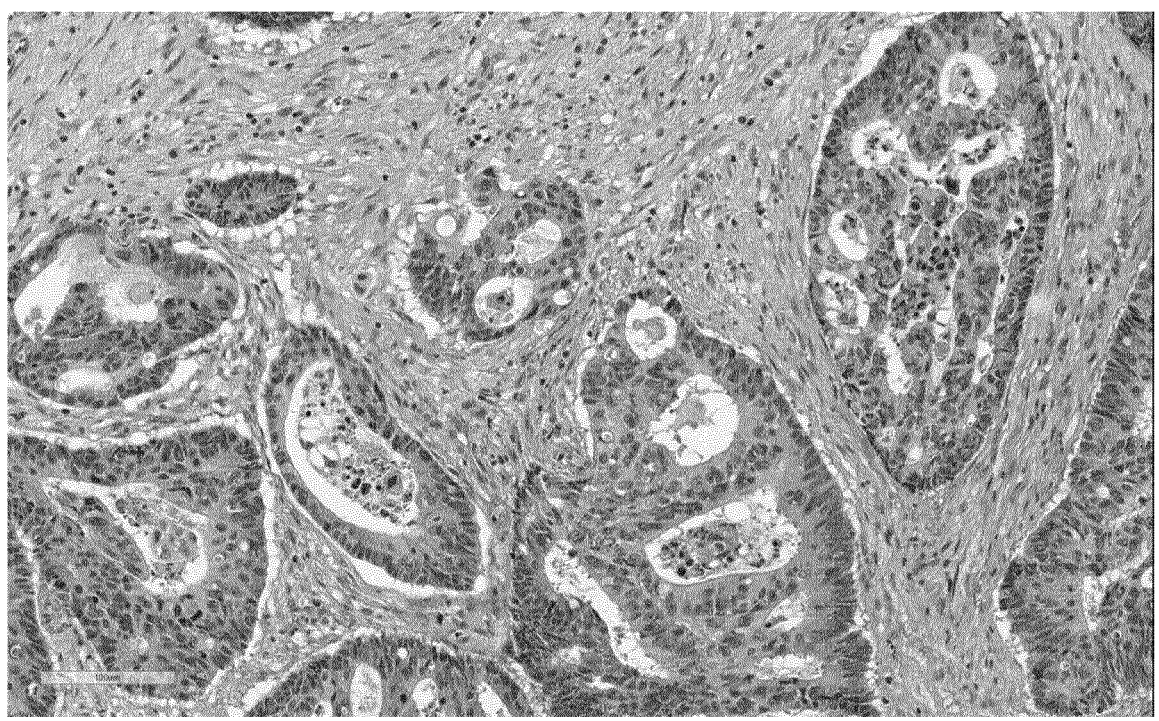
FIG. 2 shows a carcinoma of the colon fixed with Formalin.

FIG. 2. Carcinoma of the colon. Same case as above, but fixed routinarily in Formalin. The similarity in fixation and structural preservation is evident.

Example 2

40% Glyoxal deprived of acids, prepared using an ion exchange resin (Amberlite® IRA-400 chloride form), according to the described procedure, was immediately frozen at −20° C. As an alternative, glyoxal was mixed with phosphate buffer pH 7.4 and frozen at −20° C.

These samples were kept frozen for 3 months, then thawed and used for preparing a fixing solution containing 2% Acid-free Glyoxal in phosphate buffer 0.1M pH 7.3. This reagent was used for fixing tissues as described in Example 1. The results confirmed a very good fixation, thus confirming that freezing prevents acidification of the fixative leading to worsening of the fixation properties.

Example 3

Tissue samples of colon carcinoma were selected, as in example 1, and fixed in the following liquids; 1) 4% Formaldehyde in phosphate buffer pH 7.4 0.1 M (Diapat, Bergamo), 2) 2% Acid-Free Glyoxal in phosphate buffer pH 7.3 0.1M 3) 2% Acid-Free Glyoxal in NaCl 0.9% pH 7.2-7.4; 4) 2% Acid-Free Glyoxal in phosphate buffer pH 7.3 0.1M preserved in the "Bag in Box" container; 5) 2% Acid-Free Glyoxal in phosphate buffer pH 7.3 0.1M preserved in the "Seal-SAFE" bag.

While fixative N. 2 and 3 were used immediately after preparation, fixatives N. 4 and 5 were kept in air-tight conditions up to 3 months.

Results.

The histological examination of the samples fixed in the different types of fixatives, while confirming the optimal preservation in tissues fixed in fixatives N. 2 and 3, similar to that obtained in tissues fixed in formalin (Fixative N.1), showed that prevention of the exposure to air, using the Bag-in-box or the under-vacuum procedures, preserves the fixation properties of the Acid-Free Glyoxal fixative, by preventing oxidation and formation of glyoxylic acid.

Figure 3:
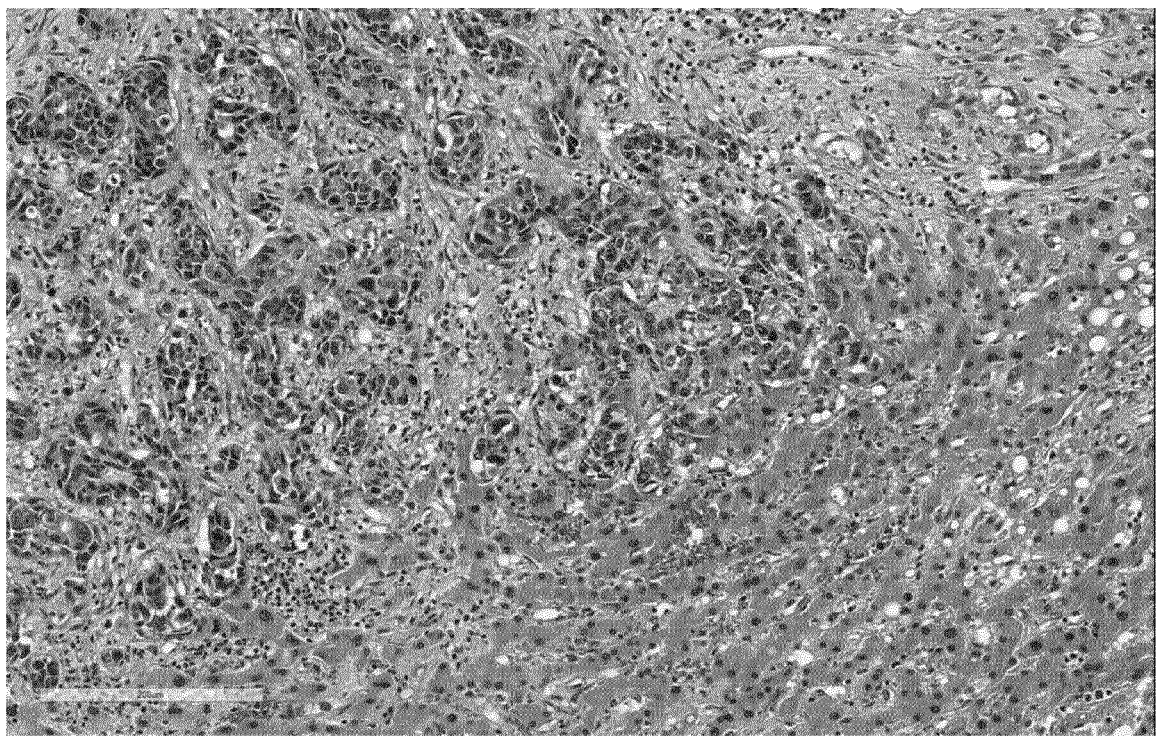
FIG. 3 shows the liver metastasis of a colon carcinoma after fixation with Acid Free Glyoxal.

FIG. 3. Liver metastasis of a colon carcinoma. Fixation in 2% Acid-Free Glyoxal in phosphate buffer pH 7.3 0.1M. The optimal preservation of the structure is evident. Erythrocytes are visible In hepatic sinusoids, confirming the lack of lyses.

Figure 4:
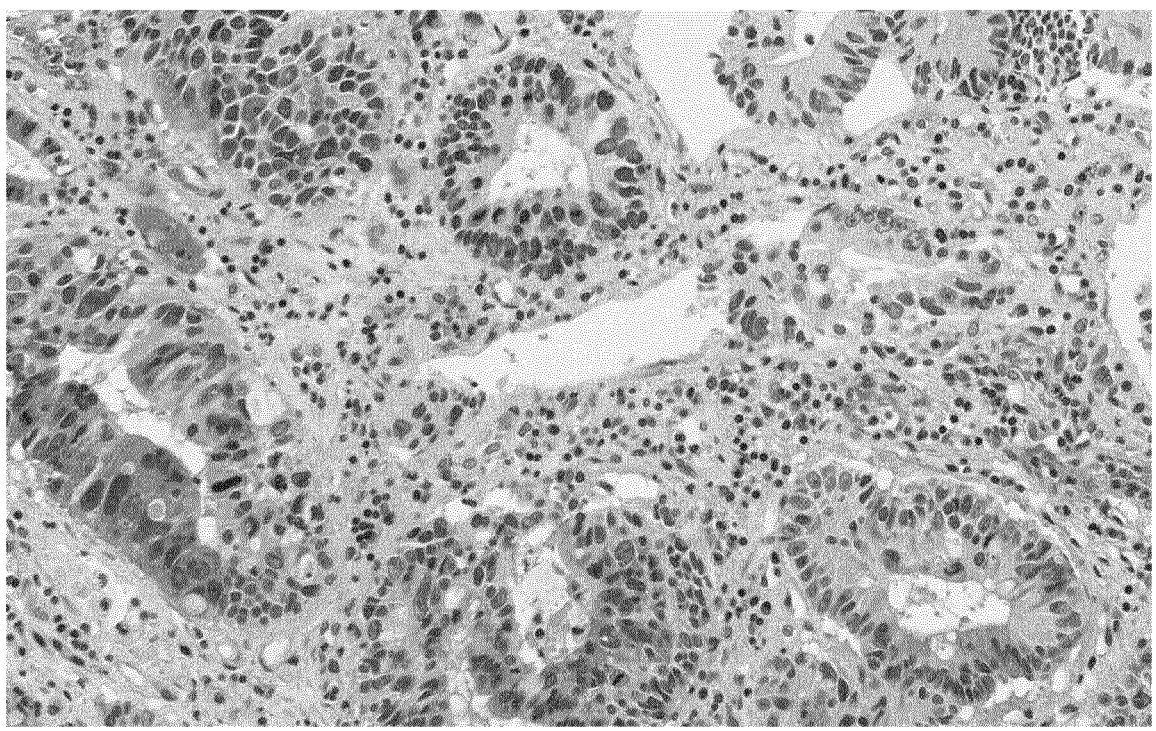
FIG. 4 shows a carcinoma of the colon after fixation with Acid Free Glyoxal.

FIG. 4. Carcinoma of the colon. Fixation of Acid Free Glyoxal. In the stroma, erythrocytes and eosinophylic leucocytes are visible.

Example 4

In order to deprive glyoxal of acids in order to obtain Acid-Free Glyoxal (GAF), the following procedure was followed: 250 g of Amberlite® IRA-400 chloride form, a strongly basic ion-exchange resin (Sigma-Aldrich) was moistened with de-ionized $H_2O$, then activated by a short wash with NaOH 1 M. After several washes in water in order to remove sodium hydroxide, 150 ml of glyoxal were added. The resin was allowed to act for 30 min, at room temperature, and then removed by passage through a filter. The resulting, water-clear liquid whose pH is around neutrality represented 40% glyoxal deprived of acids (GAF). A 2% solution of GAF was used as the fixative of choice.

A 2% GAF solution in 0.1 M phosphate buffer pH 7.3 is stable for a few weeks, then gradually undergoes oxidation producing an acidic reagent with sub-optimal fixation properties. In order to overcome the stability problem, a mother solution containing 20% GAF in 50% ethanol (Carlo Erba, Milan, Italy) was prepared and with the addition of 0.1 g calcium carbonate (Sigma-Aldrich) in 100 ml of the solution (mother solution). Alternatively, ethanol was substituted by other alcohols, such as methanol. The final (working) solution employed as GAF fixative was obtained by diluting the mother solution 1:10 in 0.11 M phosphate buffer pH 7.3.

The study included a series of surgical samples arriving fresh from the surgical theatre and harbouring a lesion of adequate dimensions (>2 cm) to allow multiple sampling in parallel. Eight cases of colorectal adenocarcinomas were sampled according to standard practice and fixed in parallel in Phosphate buffered formalin (PBF) and in GAF (working solution).

Following overnight fixation at RT, dehydration in alcohol and paraffin embedding followed standard procedures to paraffin embedding with an automatic processor (Leica ASP 300, Leica Microsystems, Wetzlar, Germany). Sections of the 8 cases were stained in Haematoxylin and Eosin (H&E) and processed for molecular analyses.

For the study of DNA sequences, nine sections (5 µm-thick) were obtained from paraffin-embedded tissue blocks of 25 colorectal adenocarcinomas. Specimens, selected and processed in parallel, were fixed in GAF and in PBF. Sections were deparaffinized using 1 ml of xylene. After over-night incubation at 56° C. with proteinase K, DNA was isolated from five sections using the MagCore Genomic DNA FFPE kit on the MagCore automatic extractor instrument (RBC Bioscience, New Taipei City, Taiwan) according to manufacturer's protocol.

DNA extracts were quantified by Qubit BR assay on Qubit Fluorometer (Invitrogen, Carlsbad, Calif., USA) and NanoDrop Spectophotometer (ThermoFisher Scientific).

DNA integrity was evaluated with Agilent 2100 Bioanalyzer (Agilent Technologies, Santa Clara, Calif.), using DNA high sensitivity reagents on DNA HS chip. Samples were diluted at 2 ng/µL and DNA length analysis was performed according to manufacturer's instruction.

For direct DNA sequencing, a total of 50 ng of DNA was amplified for the exon 2 of KRAS (246 bp) using the following PCR condition: 1× buffer, 2.5 mM MgCl2, 0.4 µM of forward and reverse primers (forward: 5'-GGTGGAGTATTTGATAGTGTATTAACC-3' SEQ ID NO:1 and reverse: 5'-AGAATGGTCCTGCACCAGTAA-3', SEQ ID NO:2), and 0.2 unit of Taq Polymerase in a final volume of 25 µL. PCR reactions were carried out with the following touchdown program: 94° C. for 2 minutes, followed by 3 cycles of 94° C. for 15 seconds, 64° C. for 30 seconds and 70° C. for 30 seconds; 3 cycles of 94° C. for 15 seconds, 61° C. for 30 seconds and 72° C. for 30 seconds; 3 cycles of 94° C. for 15 seconds, 58° C. for 30 seconds and 72° C. for 30 seconds; 35 cycles of 94° C. for 15 seconds, 57° C. for 30 seconds and 72° C. for 30 seconds, with a final extension of 70° C. for 5 minutes. PCR templates were visualized by electrophoresis on 3% agarose gel, and purified with ExoProStar (GE Healthcare, Milan, Italy) for the subsequent sequencing analyses. A final 15 ng of PCR products were purified with the ExoProStar and used for sequencing analyses. A cycle-sequencing PCR reaction was set up using the Big Dye Version 3.1 Terminator cycle-sequencing kit (ThermoFisher Scientific), with the same amplifying primer added to a final concentration of 5 pmol/µL in a volume of 20 µL. The cycling conditions were: 25 cycles at 96° C. for 10 seconds, 50° C. for 5 seconds, and 60° C. for 4 minutes; the reaction was terminated at 4° C. The cycle sequencing products were purified using Agencourt CleanSEQ (Beckman Coulter, California, USA), and the DNA was sequenced using an automated 16 capillary sequencer (3730 DNA Analyzer, Applied Biosystems, California, USA).

For pyrosequencing, KRAS exon 2 was amplified and sequenced in order to evaluate the status of codon 12 and 13 by pyrosequencing, which is a method based on "sequencing by synthesis" principle, using PSQ 96 (Qiagen, Hilden, Germany). DNA amplification was performed with the following primers: forward 5'-GGCCTGCTGAAAATCACG-3', SEQ ID NO:3, reverse 5' biotin-GCTCTATCGT-CATGGCTCT-3', SEQ ID NO:4 (size 80 bp). After denaturation at 94° C. for 5 minutes, DNA samples underwent to 40 cycles at 94° C. for 45 seconds, 57° C. for 45 seconds and 72° C. for 1 minute, and a final elongation at 72° C. for 5 minutes; the 5'-biotinylated PCR products were bound onto streptavidin-coated paramagnetic beads (GE Healthcare), denatured by 0.1 mol/1 NaOH and released according to the manufacturer's instructions using Pyro-Mark Vacuum Prep Workstation (Qiagen). These reactions were performed in a 96-wells plate using Pyro Gold Reagents (Qiagen). The primed single-stranded DNA templates were subjected to real-time sequencing of the region including codon 12 and 13 by using the sequencing primer 5'-CTTGTGGTAGTTGTAGCT-3', SEQ ID NO:5. The obtained pyrograms were analyzed by using PyroMark ID Software v 1.0 (Qiagen).

The PBF-fixed samples of the 8 colorectal adenocarcinomas collected in the study had been routinely subjected to Sequenom MassARRAY® to screen for KRAS mutations and six were found to harbour a KRAS mutation. The DNA corresponding to parallel PBF- and GAF-fixed samples of 8 colorectal cancer cases (6 KRAS mutant and 2 wild-type according to the previous test) were then subjected to direct sequencing, pyrosequencing and Sequenom MassARRAY®. The pathogenic KRAS mutations affecting codon 12 previously identified in the PBF-fixed specimens were all confirmed in the GAF-fixed samples. By both techniques the specific KRAS mutation detected in each specimen showed a mutant allele frequency that was comparable to that detected in PBF-fixed mirror samples (Table).

TABLE

KRAS exon 2 sequencing analysis with different techniques on parallel samples (GAF-fixed and PBF-fixed).

| Sample ID | KRAS exon 2 SANGER | | | | KRAS exon 2 PYROSEQUENCING | | KRAS exon 2 SEQUENOM | |
|---|---|---|---|---|---|---|---|---|
| | GAF | | PBF | | | | | |
| | Forward | Reverse | Forward | Reverse | GAF | PBF | GAF | PBF |
| 1 | WT | WT | WT | WT | WT | WT | WT | WT |
| 2 | G12S | G12S | G12S | G12S | G12S | G12S | G12S | G12S |

TABLE-continued

KRAS exon 2 sequencing analysis with different techniques on parallel samples (GAF-fixed and PBF-fixed).

| Sample ID | KRAS exon 2 SANGER | | | | KRAS exon 2 PYROSEQUENCING | | KRAS exon 2 SEQUENOM | |
|---|---|---|---|---|---|---|---|---|
| | GAF | | PBF | | | | | |
| | Forward | Reverse | Forward | Reverse | GAF | PBF | GAF | PBF |
| 3 | G12C | G12C | G12C | G12C | G12C | G12C | G12C | G12C |
| 4 | G12D* | G12D | G12D* | WT | G12D | G12D* | G12D | G12D |
| 5 | G12V | G12V | G12V | N.A. | G12V | G12V | G12V | G12V |
| 6 | G12D | G12D* | G12D* | G12D* | G12D | G12D | G12D | G12D |
| 7 | G12A | G12A | G12A | G12A | G12A* | G12A | G12A | G12A |
| 8 | WT | WT | WT | WT | WT | WT | WT | WT |

GAF: Glyoxal Acid Free;
PBF: Phosphatase Buffered Formalin;
N.A.: not assessable;
WT: wild-type;
*low mutant allele frequency.

Example 5

Commercially available solutions of glyoxal contain numerous acids derived from processes of oxidation and degradation during production and storage of glyoxal (Zhiyong Zhang, Dishun Zhao and Baoyun Xu, Journal of Chromatographic Science 2013; 51:893-898). These acids are completely removed following passage in ion exchange resins, but soon after this passage, as a consequence of exposure to air, or because of degradation processes, a gradual formation of new acids take place in the fixative during storage.

An analytical evaluation of the content in these fixatives of one (and the most reactive) of these acids, i.e. glyoxylic acid, has been carried out.

The analysis was performed in solution of water containing Phosphate buffer 0.1M pF 7.4, to which commercial 2% glyoxal (original solution: 40% Glyoxal, Sigma) was added.

The addition of this small amount of glyoxal involves a decrease of the pH of the diluted solution, because of the strong acidity of the former and despite of the buffer present (Solution N.1: Prepared 1 week before the analysis).

2) Solution exactly as before, but prepared 6 months before analysis. The pH of this solution was strongly acid (pH 4.5) as the result of the progressive formation of acids due to oxidation and degradation.

3) Solution of water containing Phosphate buffer pH 7.4, 0.1M, to which 2% of Acid Free Glyoxal, prepared by passage through ion exchange resin, was added. The solution was prepared 2 months before analysis and kept frozen at −20° C.

4) A solution of water containing Phosphate buffer pH 7.4, 0.1M, was added to a 2% Acid Free Glyoxal solution, prepared by passage through ion exchange resin and 10% ethanol (Carlo Erba). The presence of ethanol, having antioxidant activity, is finalized to prevent oxidation and thus acidification of the reagent.

Conditions of Analysis.

Determination of the content in glyoxylic acid in the 4 samples was made with ionic chromatography with conductimetric determination.

The identification of the signal to be referred to glyoxylic acid was checked in front of a control represented by a standard of glyoxylic acid (Sigma). The same procedure to determine the concentration of glyoxylic acid, which can derive from the direct oxidation of glyoxal, was used.

The apparatus used for the analysis was a Dionex DX 500 ionic chromatograph. The data were recorded also using visible-UV spectra.

B. SUMMARY OF THE RESULTS

TABLE

Results of the determination of the content in glyoxylic acid in the 4 samples.

| Sample 1 0.67 ± 0.07 mM | <LOD[i] |
|---|---|
| Sample 2 37.8 ± 1.2 mM | 1.7 ± 0.2 |
| Sample 3 0.28 ± 0.05 mM | <LOD[i] |
| Sample 4 0.21 ± 0.03 mM | <LOD[i] |

[i]The detection limit (LOD) of glyoxylic acid is in the range of about $1-2 \times 10^{-3}$ mM.

Figure 5:
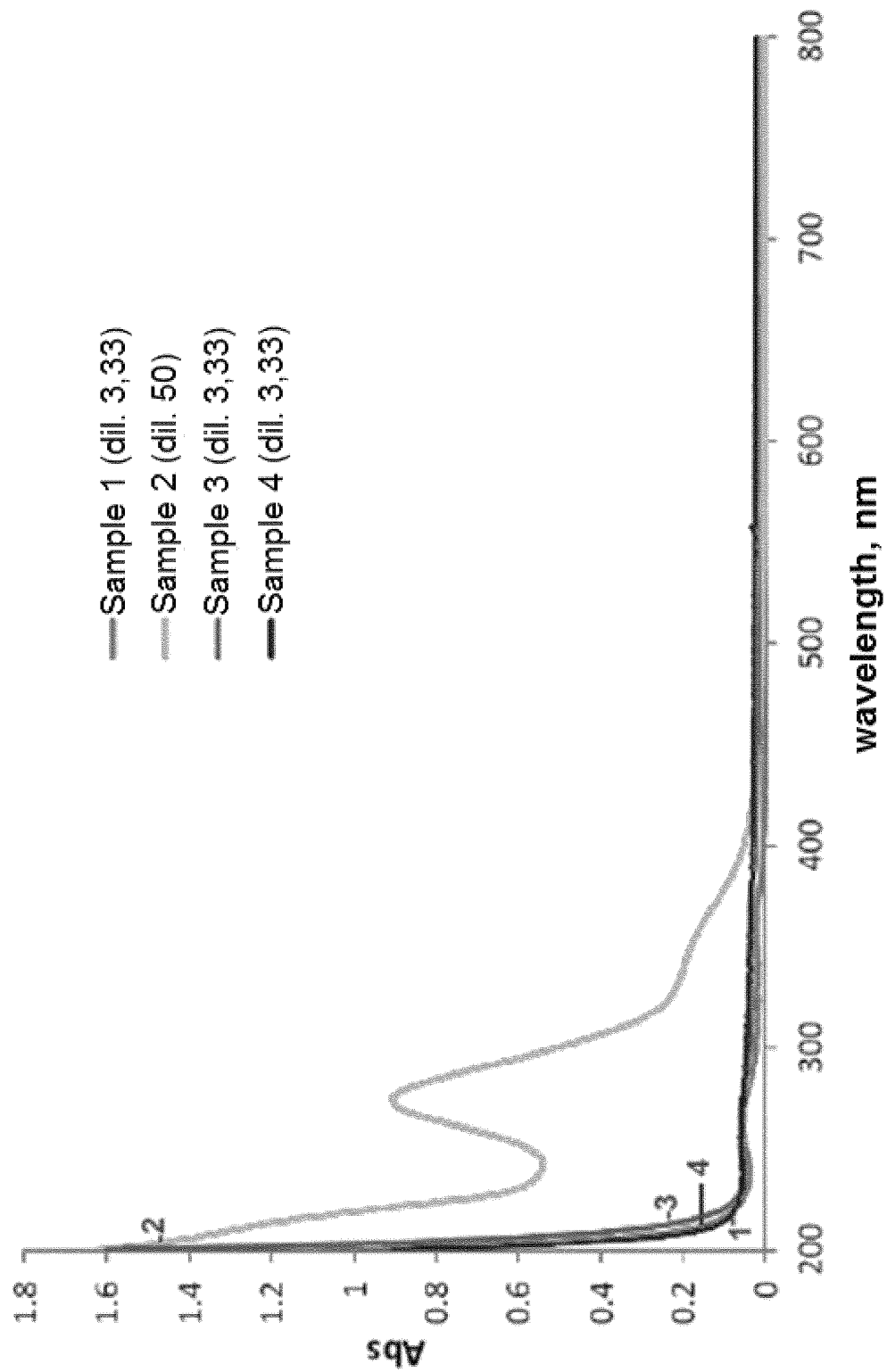
FIG. 5 shows the absorption spectra of the samples described in Example 5.

Absorption spectra of the samples (FIG. 5).

Considering that a 2% w/w glyoxal solution has a concentration of approximately 380 mM, the concentration of glyoxylic acid in Sample 2 is about 10% of the glyoxal initially present.

C) Conclusions

1) Glyoxal, in solution, undergoes a progressive oxidation and degeneration with acidification which reaches an equilibrium around pH 4-4.5 which is in fact the pH of the commercial solution of glyoxal. In Sample 2, containing glyoxal 2%, after 6 months the pH dropped to pH 4.5 and showed a very high content of glyoxylic acid.

2) Passage in ion-exchange resins (Amberlite) removed the acids, but this is soon followed by a novel formation of glyoxylic acid, whose level is however much lower than that of Sample 1 (containing commercial glyoxal). This shows that in a 2% glyoxal solution (as the one used in the fixative) a concentration of glyoxylic acid lower than 0.3 mM can only be obtained by removing acids with ion exchange resins. In fact, the concentration of glyoxylic acid in sample 1 is higher than the above limit.

3) the prevention of the oxidation and degeneration processes leading to the formation of glyoxylic acid can be obtained either by freezing the solution (Sample 3) or by adding an alcohol such as ethanol, which acts as an antioxidant agent.

The invention claimed is:

1. A method of fixing tissues comprising submerging said tissues in an aqueous solution consisting of acid free glyoxal, wherein the glyoxal solution has a concentration by weight of 2% and wherein the pH of the solution ranges from 7.0 to 7.4, wherein the solution is obtained by treatment of a glyoxal commercial solution with a basic ion-exchange resin, and frozen at −20 C. for up to two months before use.

2. The method according to claim 1 for fixing and preserving human, animal and vegetable cells and tissues for histological, cytological, immune-histochemical evaluation and for genic analysis.

3. The method according to claim 1 wherein the solution is preserved from oxidation and acidification by preventing air contact.

4. The method according to claim 3 wherein the solution is preserved from oxidation and acidification by distribution in a container "bag in box" and/or under-vacuum container.

* * * * *

SEQUENCE LISTING

<160> NUMBER OF SEQ ID NOS: 5

<210> SEQ ID NO 1
<211> LENGTH: 27
<212> TYPE: DNA
<213> ORGANISM: Artificial Sequence
<220> FEATURE:
<223> OTHER INFORMATION: forward primer

<400> SEQUENCE: 1
ggtggagtat ttgatagtgt attaacc                                           27

<210> SEQ ID NO 2
<211> LENGTH: 21
<212> TYPE: DNA
<213> ORGANISM: Artificial Sequence
<220> FEATURE:
<223> OTHER INFORMATION: reverse primer

<400> SEQUENCE: 2
agaatggtcc tgcaccagta a                                                 21

<210> SEQ ID NO 3
<211> LENGTH: 18
<212> TYPE: DNA
<213> ORGANISM: Artificial Sequence
<220> FEATURE:
<223> OTHER INFORMATION: forward primer

<400> SEQUENCE: 3
ggcctgctga aaatcacg                                                     18

<210> SEQ ID NO 4
<211> LENGTH: 19
<212> TYPE: DNA
<213> ORGANISM: Artificial Sequence
<220> FEATURE:
<223> OTHER INFORMATION: reverse primer

<400> SEQUENCE: 4
gctctatcgt catggctct                                                    19

<210> SEQ ID NO 5
<211> LENGTH: 18
<212> TYPE: DNA
<213> ORGANISM: Artificial Sequence
<220> FEATURE:
<223> OTHER INFORMATION: sequencing primer

<400> SEQUENCE: 5
cttgtggtag ttgtagct                                                     18